United States Patent
Kruusing

(10) Patent No.: US 9,030,193 B2
(45) Date of Patent: May 12, 2015

(54) MEASUREMENT SYSTEM OF FERROMAGNETIC PARTICLES

(75) Inventor: Arvi Kruusing, Lumijoki (FI)

(73) Assignee: Hemeltron, Lumijoki (FI)

( * ) Notice: Subject to any disclaimer, the term of this patent is extended or adjusted under 35 U.S.C. 154(b) by 313 days.

(21) Appl. No.: 13/522,676

(22) PCT Filed: Jan. 19, 2011

(86) PCT No.: PCT/FI2011/050040
§ 371 (c)(1),
(2), (4) Date: Jul. 17, 2012

(87) PCT Pub. No.: WO2011/089318
PCT Pub. Date: Jul. 28, 2011

(65) Prior Publication Data
US 2012/0299584 A1    Nov. 29, 2012

(30) Foreign Application Priority Data

Jan. 20, 2010 (FI) ...................................... 20105044

(51) Int. Cl.
*G01N 27/74* (2006.01)
*G01N 33/28* (2006.01)

(52) U.S. Cl.
CPC ............ *G01N 33/2888* (2013.01); *G01N 27/74* (2013.01)

(58) Field of Classification Search
CPC .............. A61N 1/00; A61N 1/40; A61N 1/44; A61N 2/006; A61N 2/008; A61N 2/02
USPC ........................... 324/204, 212–214, 258–260
See application file for complete search history.

(56) References Cited

U.S. PATENT DOCUMENTS 6,046,585 A    4/2000  Simmonds
(Continued)

FOREIGN PATENT DOCUMENTS

EP    1 262 766 A2    12/2002
(Continued)

OTHER PUBLICATIONS

International Search Report for parent application PCT/FI2011/050040, having a mailing date of May 20, 2011.
(Continued)

*Primary Examiner* — Huy Q Phan
*Assistant Examiner* — Temilade S Rhodes-Vivour
(74) *Attorney, Agent, or Firm* — Andrus Intellectual Property Law, LLP

(57) ABSTRACT

A system by which the proportion of ferromagnetic particles in a dielectric medium is measured. A magnetic field is generated by two signals in the medium: a low frequency feed and a relatively high frequency excitation. The feed magnetizes the ferromagnetic particles in the medium to the nonlinear range of the magnetization curve. The excitation is generated so that its spectrum is relatively wide and it is dense with frequency components. The level of the excitation is so high that the magnetic flux density in the medium corresponding to the excitation fluctuates nonlinearly, when the feed is at its peak value or near this. The magnetic field of the medium is measured by a secondary winding, and from the response signal produced by the sensor is detected the part resulting from the magnetic non-linearity, which part is the output signal. In the detection the response is multiplied by the signal, which arises magnetic field and includes the same random fluctuation as the response. The higher the proportion of the ferromagnetic particles in the medium is, the higher the level of the output signal. The secondary winding comprises several portions so that the parasitic voltages caused by the stray capacitances compensate each other. The measurement is real-time and accuracy, because the excitation is a random signal by nature, in which case its spectrum includes, instead of one frequency component, densely frequency components in a certain band. The result is a 20-30 dB higher signal-to-noise ratio in the response and output signal compared with the known technique. A device according to the method is suitable for use in an industrial plant and moving vehicles, in which there are interfering fields and the temperature can be high.

21 Claims, 7 Drawing Sheets

(56) References Cited

U.S. PATENT DOCUMENTS

| | | |
|---|---|---|
| 2003/0027197 A1 | 2/2003 | Nikitin et al. |
| 2004/0146849 A1* | 7/2004 | Huang et al. .................. 435/4 |
| 2004/0210289 A1* | 10/2004 | Wang et al. .................. 607/116 |
| 2005/0266478 A1* | 12/2005 | Huang et al. .................. 435/6 |
| 2007/0108320 A1* | 5/2007 | Pfeffer et al. .................. 241/5 |
| 2007/0172890 A1* | 7/2007 | Prins et al. .................. 435/7.1 |
| 2010/0159556 A1* | 6/2010 | Rida .................. 435/173.7 |

FOREIGN PATENT DOCUMENTS

| | | |
|---|---|---|
| FR | 2 920 875 A1 | 3/2009 |
| WO | 2004/077044 A1 | 9/2004 |

OTHER PUBLICATIONS

Finnish Search Report for priority application FI 20105044, dated Oct. 21, 2010.

* cited by examiner

Fig. 3a
PRIOR ART
Fig. 3b
PRIOR ART
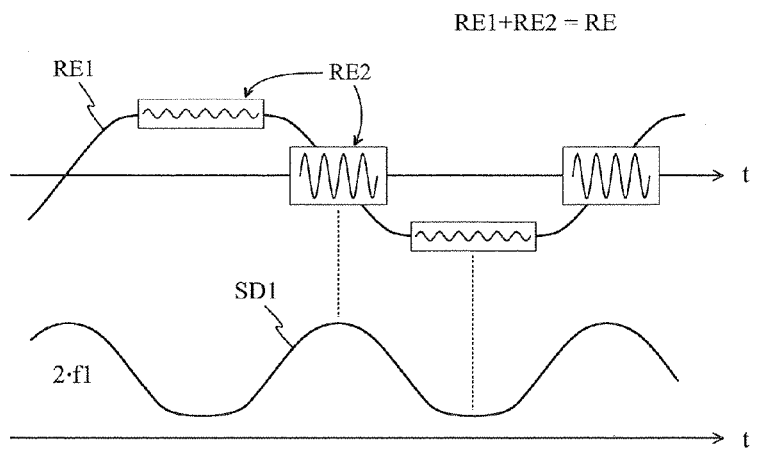
Fig. 4a
PRIOR ART
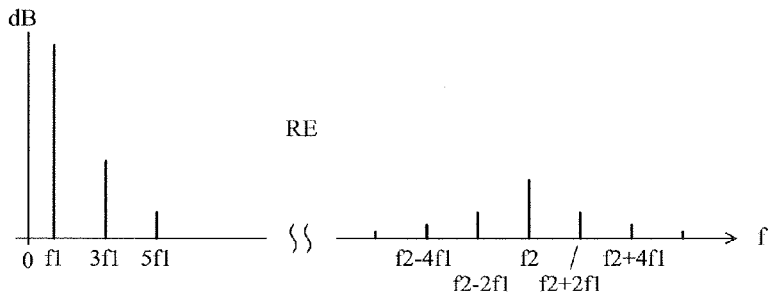
Fig. 4b
PRIOR ART
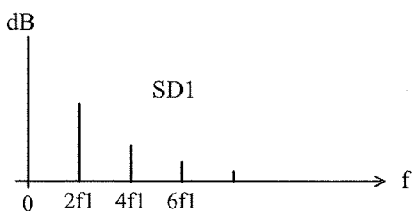

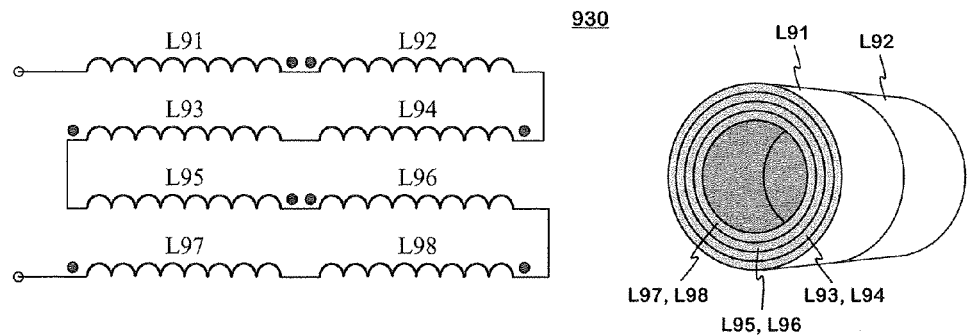
Fig. 9
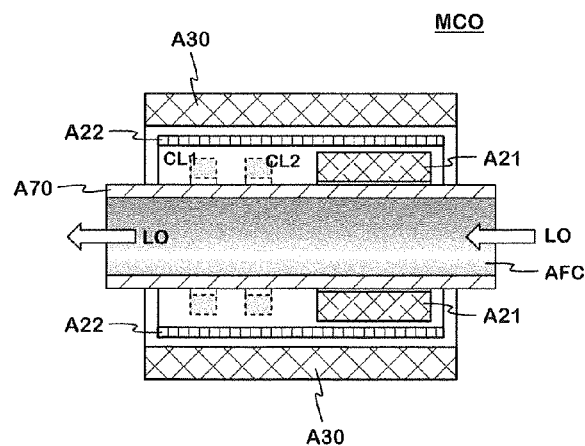
Fig. 10
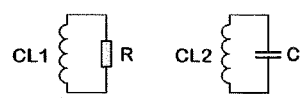

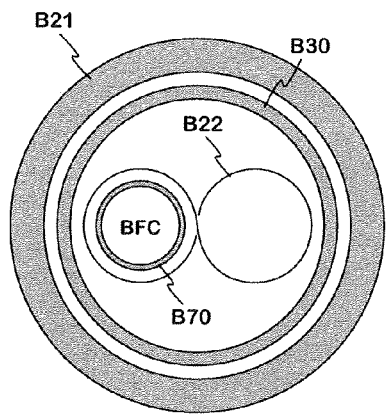 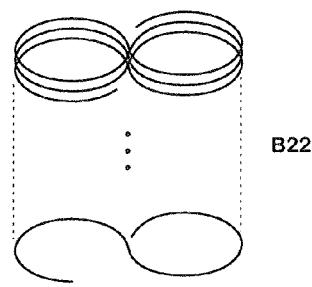
Fig. 11a  Fig. 11b
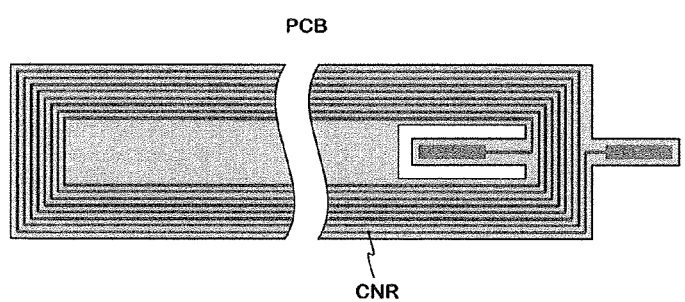 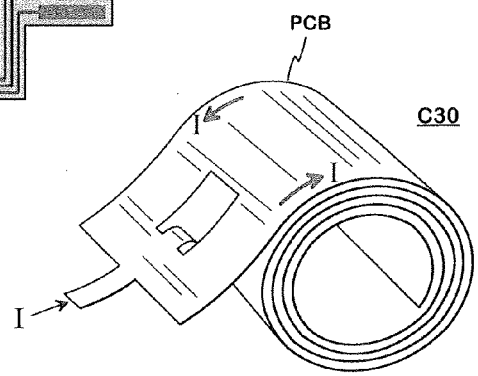
Fig. 12a  Fig. 12b

US 9,030,193 B2

MEASUREMENT SYSTEM OF FERROMAGNETIC PARTICLES

CROSS-REFERENCE TO RELATED APPLICATIONS

This application is the U.S. national stage application of International Application No. PCT/FI2011/050040, filed Jan. 19, 2011, which International application was published on Jul. 28, 2011 as International Publication No. WO 2011/089318 A1 in the English language and which application is incorporated herein by reference. The International application claims priority of Finnish Patent Application No. 20105044, filed Jan. 20, 2010, which application is incorporated herein by reference.

BACKGROUND

The invention relates to a system, by which the proportion of ferromagnetic particles in a dielectric medium is measured. The primary object is to monitor the purity of lubricating oil in respect of the particles which have got into it in consequence of metal wearing. The measurement system includes both the method and arrangement for realizing it.

As known, the lubricating oil is a necessary medium in the gears, where the metal surfaces move in respect of each other, to reduce friction and to prevent excessive heating up. Such gears are i.a. different motors, power trains and actuators, and for example rolling lines, process lines of paper machines and printing machines as well as machines in the power plants. The order of magnitude of the lubricating oil's consumption in the world is ten million cubic meters per annum.

During use the lubricating oil degrades because of contamination, and eventually it is unsuitable for its aim. The particles loosen from a gear constitute the most of the contaminants, as much as 95%. The proportion of such particles in the lubricating oil is the best indicator of the gear wear condition. For this reason the information about the wear particle proportion is very useful, when it is striven to avoid failure of a gear and the costs caused by it.

At least the following methods can in principle be used for the measurement of the wear particle proportion:

Ferrography, in which an oil sample is driven through a static magnetic field, in which case the iron particles with different size move different distances. The result is examined by a special microscope. The measuring equipment is relatively expensive and susceptible to external interferences.

Emission spectroscopy, in which an oil sample is for example heated strongly, and thereafter the spectrum of the radiation, which comes from the sample, is measured. As known, different materials, like iron, radiate at different frequencies and are seen in the spectrum. The measuring equipment is relatively expensive.

Neutron activation analysis, in which an oil sample is bombarded by neutrons so that the wear particles in it become radioactive for a time. The proportion of the particles can be deduced from the radiation which they transmit. The method is accurate, but it requires an expensive measuring equipment and is slow.

Optical method, in which the scattering of the light from an oil sample is examined. The measuring equipment is expensive and is not valid, when the oil is dark.

The method of the linear magnetic response, in which ferromagnetic particles in an oil sample are magnetized in the linear range of the magnetization curve. The impedance of the coil, by which the magnetization is implemented, rises a little when the amount of the ferromagnetic material increases. This impedance is converted into an output quantity which then in principle gives the particle proportion. A flaw of the method is its unsatisfactory sensitivity; when the particle proportion is low, the measurement signal does not stand out in the noise.

The method of the nonlinear magnetic response, in which the inductive coupling between the sending and receiving elements belonging to the measuring equipment is changed by saturating magnetically the ferromagnetic particles in an oil sample. The measurement signal, the level of which depends on the particle proportion, is obtained by processing the receiving signal.

The last-mentioned method is applied in the invention, which method has proved most suitable for most of the practical requirements. Let us consider the method first in the theory level: FIG. 1 shows the very well known magnetization curve of the ferromagnetic materials in HB coordinates. Quantity H is the strength of the magnetic field, which falls from outside into a ferromagnetic material, and quantity B is the magnetic flux density in said material. When quantity H starts to rise from zero, quantity B rises first linearly and relatively steeply when the ferromagnetic material polarizes step by step to the direction of the magnetic field. After the polarization has completed, or the material has saturated magnetically, the magnetic flux density B rises only very gently, when quantity H still is strengthened. The ratio B/H is the permeability p, or magnetic conductivity. If a ferromagnetic object is a part of a magnetic circuit, which comprises a primary and secondary winding, the mutual inductance and coupling between the windings depend on the permeability. When the signal level is low, the coupling coefficient is constant, but when using higher signal levels it decreases, if the ferromagnetic material is now and then in saturation. The derivative dB/dH of the curve, or the dynamic permeability $\mu_d$, gives the magnetic conductivity, when the magnetic field strength H fluctuates in a relatively narrow range near an operating point. In FIG. 1 the operating point WP1 is in the linear range, where the dynamic permeability is relatively high. The operating point WP2 again is in the nonlinear range, where the dynamic permeability is low. Let us assume that a ferromagnetic material is magnetized to a certain operating point and an alternating current with relatively low constant amplitude is fed to the primary. Then, in the case of said operating point WP2 a clearly lower alternating voltage induces to the secondary winding than in the case of the operating point WP1 because of weakening of the coupling.

FIG. 2 shows as a block diagram a system, known from the publication WO 2004/077044, for measuring the proportion of ferromagnetic particles, which system utilizes the nonlinear magnetic response. The system comprises a low frequency source G1 and an excitating source G2, a magnetizing winding 211, an excitating winding 212 and a secondary winding 220, a first 230 and second 240 detector as well as a frequency multiplier 250. The medium LO, the particle proportion of which is measured, is in a dielectric vessel in the middle of the windings.

The low frequency source G1 generates a sinusoidal feed FD, the frequency f1 of which is in the range of 50-100 Hz, and the excitating source G2 generates a sinusoidal excitation EX, the frequency f2 of which is in the range of 10-100 kHz. The current of the low frequency source is led to the magnetizing winding 211, and the magnetic flux arising in this winding flows through the medium LO and secondary winding 220. The magnetic field of the magnetizing winding is so strong that the ferromagnetic particles in the medium saturate during its peaks. The current of the excitating source G2 is led to the excitating winding 212, and the magnetic flux arising in this winding flows through the medium LO and secondary winding as well, being summed with the magnetic flux of the magnetizing winding. The magnetic field strength of the excitating winding is at least one order lower than the magnetic field strength of the magnetizing winding by amplitude.

The secondary winding 220 outputs the response RE, which is detected coherently in the first detector 230 by using the excitation EX as a 'carrier'. The detecting result SD1 of the response is detected coherently in the second detector 240 by using a 'carrier', the frequency of which is 2·f1. This subcarrier is generated from the feed FD by the frequency multiplier 250. The second detecting result, or the output signal SD2, shows then the amplitude of the signal SD1, more exactly the amplitude of the component with the frequency 2·f1. In principle, also envelope detectors could be used as detectors, but in that case the signal-to-noise ratio in the output signal would be poorer than when using coherent detectors. In both cases filters belong to the detectors, by which filters excess parts are removed from the signal spectra.

FIG. 3a shows the response RE in the time domain, its principled waveform. The response RE is a sum of two response components. The first response component RE1 is the voltage induced in the secondary winding by the feed FD. Because of the saturation of the ferromagnetic particles the first response component is not sinusoidal but flattened at its peaks. The second response component RE2 is the voltage induced in the secondary winding by the excitation EX. Its amplitude depends on the dynamic permeability $\mu_d \neq \Delta B/\Delta H$. When the feed FD is close to the zero level corresponding to the first operating point WP1 in FIG. 1, $\mu_d$ and the second response component RE2 are relatively high. When the feed FD is in the peak range corresponding to the second operating point WP2 in FIG. 1, $\mu_d$ and the second response component are relatively low.

FIG. 3b shows the detecting result SD1 of the response in the time domain. It follows the fluctuation of the amplitude of the second response component RE2 by shape. The fundamental frequency of the signal SD1 is 2·f1, because the second response component has a minimum at both the positive and negative peak of the feed FD and a maximum at each zero point.

As mentioned, the output signal SD2 is detected from the signal SD1 using a subcarrier with the frequency 2·f1. The filtered detecting result is a straight line in the time domain. If the medium were pure of the ferromagnetic particles, it would be magnetically linear, in which case the level of the output signal SD2 would be zero. When the particle proportion increases, also the level of the output signal rises. This dependence is linear. The magnetizing feed FD has a certain optimum amplitude in respect of the quality of the output signal.

FIG. 4a shows the response RE in the frequency domain, its principled spectrum. The first response component RE1 causes to the spectrum a frequency component at point f1 and odd harmonics of this frequency component. The second response component RE2 causes to the spectrum a frequency component at point f2 and on its each side a sideband, in which the spacing between the frequency components is 2f1. These sidebands as well as the harmonics of the component with the frequency f1 are naturally a result of the distortion in the response RE due to the magnetic non-linearity of the medium.

FIG. 4b shows the detecting result SD1 of the response in the frequency domain. Because the correctly phased excitation EX is used as the subcarrier, the result is a baseband signal corresponding to said sidebands, the fundamental frequency of which signal is 2f1. The spectrum of the output signal SD2 detected from the signal SD1 is then a mere DC component after the low-pass filtering.

The above-described method applies two sinusoidal feeds with different frequencies. The term 'two-frequency method' is used for it and other corresponding ones. They are selective to the ferromagnetic wearing particles, and e.g. the oil darkness level has no meaning. A drawback of the two-frequency methods is that their accuracy is not sufficient in an environment, where there are interfering fields. Such circumstances may prevail in an industry plant and moving vehicles. Here it must be noticed that FIGS. 3a-4b show the matter very ideally. In practice the amount of the ferromagnetic material in a medium is very slight, in which case the actual signal corresponding to the excitation is in danger of vanishing into the interferences and noise. Another serious drawback is that the stray capacitance between the windings causes in the secondary winding a voltage with frequency f2, the amplitude of which is high, for example one thousand times the amplitude of the voltage being caused by the magnetic non-linearity. The elimination of this kind of interfering voltage, which is called parasitic voltage in this description, from the measuring result is difficult.

SUMMARY

An object of the invention is to reduce the drawbacks related to prior art.

The basic idea of the invention is the following: A magnetic field is generated by two signals in the medium to be measured: a low frequency feed and a relatively high frequency excitation. The feed magnetizes the ferromagnetic particles in the medium to the nonlinear range of the magnetization curve. The excitation is generated so that its spectrum is relatively wide and it is dense with frequency components. The level of the excitation is so high that the magnetic flux density in the medium corresponding to the excitation fluctuates nonlinearly, when the feed is at its peak value or near this. The magnetic field of the medium is measured by a sensor, and from the response signal produced by the sensor is detected the part caused by the magnetic non-linearity, which part is the output signal. In the detection the response is multiplied by the signal, which generates magnetic field and includes the same random fluctuation as the response. The higher the proportion of the ferromagnetic particles in the medium, the higher the level of the output signal. The sensor is a secondary winding with several portions so that the parasitic voltages caused by the stray capacitances compensate each other.

An advantage of the invention is that the accuracy and sensitivity of the measurement of the proportion of the ferromagnetic particles are better than in the known methods. This is due to the fact that the excitation is a random signal by nature, in which case its spectrum includes, instead of one frequency component, densely frequency components in a certain band. The result is a 20-30 dB higher signal-to-noise ratio in the response and output signal compared with the known technique. This further results in that a device according to the method is suitable for use in an industrial plant and moving vehicles, in which there are strong interfering fields with different frequencies. A further advantage of the invention is that the measurement is a real-time one, in which case the wearing of the metal surfaces and machine parts, which wearing is indicated by the particle proportion, can be monitored continuously. This brings savings in the maintenance costs. A further advantage of the invention is that the method according to it is selective to the wearing particles, and the possible darkness of the medium does not matter. A further advantage of the invention is that the parasitic voltage in the response can be eliminated. This is due to the above-mentioned structure of the secondary winding. In addition, a harmonic frequency of the frequency of said carrier can be used in the detection, at which harmonic frequency a parasitic voltage does not occur. A further advantage of the invention is that the measuring device according to it is relatively simple and cheap.

BRIEF DESCRIPTION OF THE DRAWINGS

In the following, the invention will be described in detail. Reference will be made to the accompanying drawings, in which

FIGS. 3a,b present in the time domain signals produced by the system according to FIG. 2;

FIGS. 4a,b present in the frequency domain signals produced by the system according to FIG. 2;

FIG. 9 presents a second example of the gradiometric winding belonging to the arrangement according to the invention;

FIG. 10 presents a second example of the measuring component belonging to the arrangement according to the invention;

FIGS. 11a,b present a third example of the measuring component belonging to the arrangement according to the invention;

FIGS. 12a,b present another example of the gradiometric winding applicable in the arrangement according to the invention;

DETAILED DESCRIPTION OF THE DRAWINGS

FIGS. 1-4b were already explained in connection with the description of the prior art.

Figure 1:
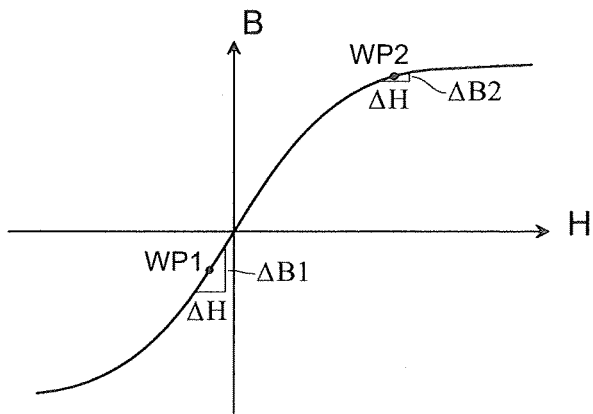
FIG. 1 presents the magnetization curve of the ferromagnetic materials.
Figure 2:
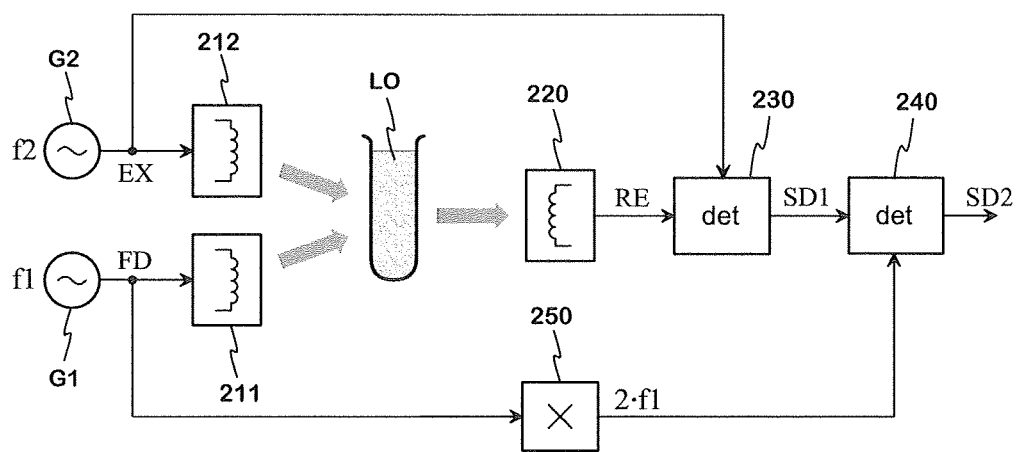
FIG. 2 presents as a block diagram an example of the system according to the prior art, which system utilizes the nonlinear magnetic response.
Figure 5:
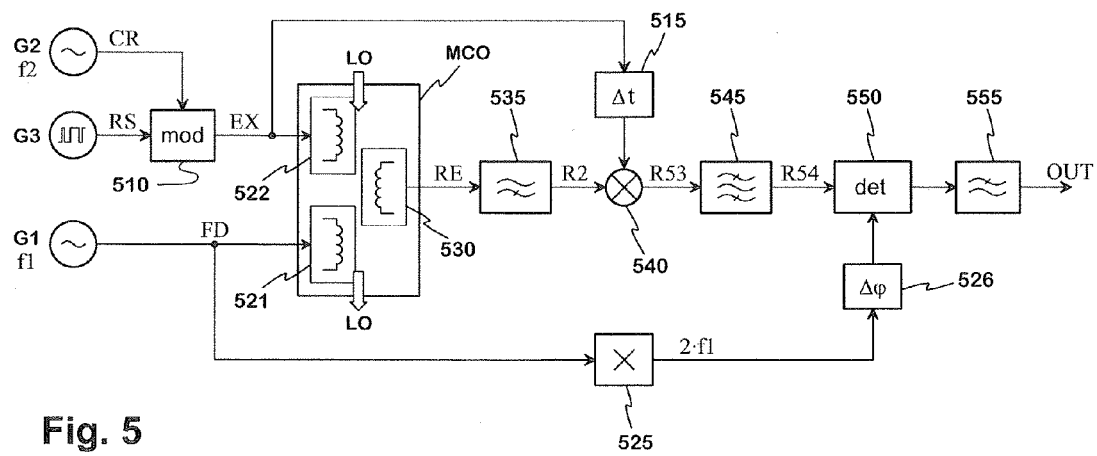
FIG. 5 presents as a block diagram an example of the arrangement according to the invention.

FIG. 5 shows as a block diagram an example of the arrangement according to the invention. It comprises a measuring component MCO and its feeding units as well as the processing units of the response. The electric part of the measuring component comprises the magnetizing winding 521, the excitating winding 522 and the secondary winding 530. The medium LO, in practice lubricating oil, flows through the measuring component.

The feeding units comprise three signal sources and a modulator. The first source G1, or the low frequency source, generates the feed FD, which is here sinusoidal. The low frequency source G1 is connected to the magnetizing winding 521, and the magnetic flux arising in this winding flows through the space confined by the medium LO and the secondary winding 530. The feed magnetizes during its peaks the ferromagnetic particles in the medium to the nonlinear range of the magnetization curve. The second source G2, or the high frequency source, generates a 'carrier' CR, which is led to the carrier input of the modulator 510. The third source G3 generates a random signal RS, which is led to the modulating input of the modulator 510. The output signal of the modulator is the excitation EX, which is then created from two signals. The modulation is for example frequency modulation with a relatively high modulation index. Irrespective of the modulation type the excitation is created to be a relatively wideband one and at least nearly continuous so that it has frequency components densely. The level of the excitation is set so that the magnetic flux density in the medium corresponding to the excitation fluctuates very nonlinearly, when the feed is at its peak value or near this. The excitation is led to the excitating winding 522, and the magnetic field arising in this winding is summed with the magnetic field of the magnetizing winding.

In this description and claims the epithet 'high frequency' is used for the excitation EX only to make a distinction to the frequency of the feed FD. In practice the frequency of the carrier CR is e.g. 50 kHz, hence not very high. The frequency f1 of the feed is e.g. 75 Hz. The epithet 'random', again, encompasses in this description and claims also the epithet 'pseudorandom'.

The secondary winding 530 sensing the magnetic field produces the response signal, or more briefly the response RE. The response includes a part, which is proportional to the rate of change of the magnetic flux density in the medium, and a part with interfering nature due to the stray capacitance between the windings. The secondary winding is connected to a high-pass filter 535, which attenuates the low frequency components in the response. The output of the high-pass filter is connected to one input of an analog multiplier, or more briefly multiplier 540. The excitation EX is led to the other input of the multiplier through a delay unit 515. In this the excitation is delayed by the same amount as the delay that the measuring component MCO and the high-pass filter 535 cause in the excitation. Thus the excitation is multiplied by its distorted and noisy form. The resulting multiplication signal R53 includes a low frequency part due to the distortion and high frequency parts. The latter ones are removed to a bandpass filter 545, to which the output of the multiplier 540 is connected. The bandpass filter 545 produces the actual signal R54, which is led to the signal input of a detector 550. A carrier for the detector 550 is generated from the feed FD by means of a frequency multiplier 525 and phase shifter 526. The frequency multiplier, which includes also a bandpass filter with the centre frequency of 2f1, produces a sine wave with this frequency, the phase of which sine wave is tuned by the phase shifter to the same one as the phase of the component with frequency 2f1 in the actual signal R54. The output of the detector 550 is connected to a low-pass filter 555, which removes all frequency components proper from the output signal of the detector and passes only the direct, or DC, component. This is the second detecting result OUT, which is also the output signal of the measuring arrangement.

No amplifiers are marked visible in the principled FIG. 5. Such are naturally needed in different points on the receiving side. Instead of the secondary winding, also for example a hall sensor or spinTJ (tunnel junction) sensor can be the sensor in the measuring component MCO, but a winding is most practical.

Figure 6A:
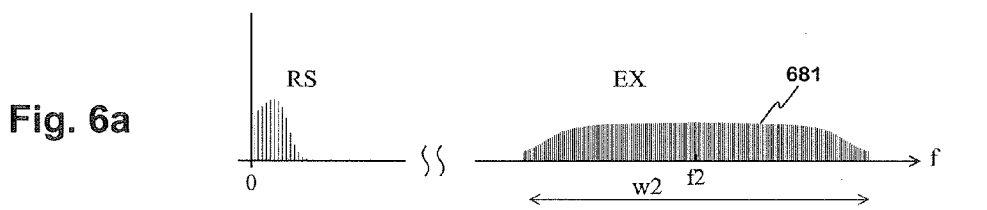
FIGS. 6a-c present in the time domain signals produced by the system according to FIG. 5.

FIG. 6a shows an example of the frequency domain presentation of the random signal RS and excitation EX, i.e. of their spectrum. The random signal RS generated by the third source G3 fluctuates so that its spectrum includes numerous frequency components. The spectrum 681 of the excitation is located symmetrically in respect of the carrier frequency f2, and its width w2 is notably greater than the width of the spectrum of the signal RS. The density of the frequency components in the spectrum 681 is high, i.e. the spectrum is in effect continuous. This is due to the nature of the random signal and the modulation.

Figure 6B:
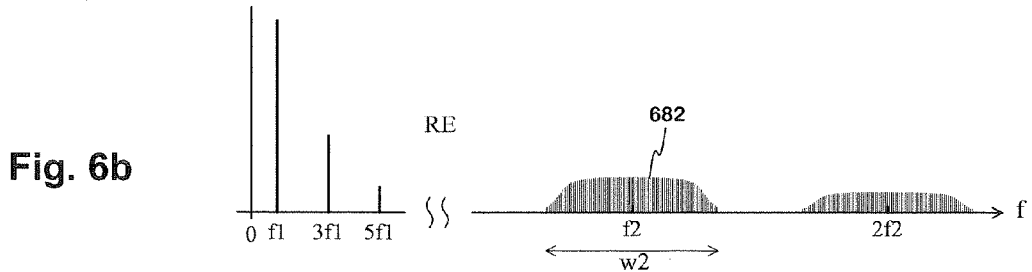

FIG. 6b shows an example of the spectrum of the response RE. It includes a part produced directly by the feed FD and another part produced by the excitation EX. The former one includes a frequency component at the feed frequency f1 and odd harmonics of this frequency component because of the magnetic non-linearity of the medium. The part produced by the excitation includes a section 682 round the frequency f2, which has the width of the original spectrum 681. In addition, there are harmonics of this section, i.e. spectra round the frequencies 2f2, 3f2 etc. with the same width, due to the distortion of the excitation because of the ferromagnetic particles in the medium.

Figure 6C:
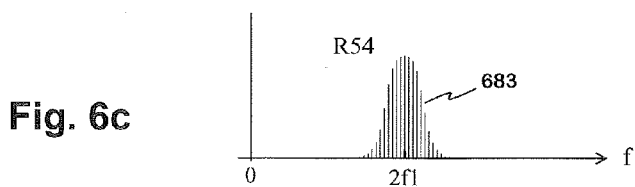

FIG. 6c shows an example of the spectrum of the actual signal R54. The multiplier 540 produces a signal, the spectrum of which includes relatively narrowband sub-spectra round the even multiples of the frequency f1 of the feed FD. These are due to the magnetic non-linearity of the medium: The part of the response corresponding to the excitation has a minimum at both the positive and negative peak of the feed and a maximum at each zero point, as in the case of the sinusoidal excitation presented in FIG. 3a. The bandpass filter 545 retains from the spectrum of the multiplier's output signal, or multiplication signal R53, only the section 683 near the frequency 2f1, which is the spectrum of the actual signal R54.

If the medium LO were magnetically linear, no fluctuation depending on the phase of the feed would occur in the response, and the section 683 round the frequency 2f1 would not exist at all in the spectrum of the multiplier's output signal. In this case the level of the actual signal R54 as well as the output signal OUT would be zero. The more ferromagnetic particles there are in the medium, the higher the level of the actual signal and the output signal.

FIGS. 6b and 6c present a noiseless case. In practice, the signals are naturally noisy. When the proportion of the ferromagnetic particles is low enough, for example less than $10^{-8}$, the spectrum 683 seen in FIG. 6c vanishes into the noise, and no output signal indicating the proportion of particles is obtained from the actual signal R54. By the use of a wideband excitation the noise level in the actual signal can be lowered compared to the two-frequency method, and thus the sensitivity of the measuring system can be improved. In addition, the effect of the strong but narrowband interferences caused for example by the electrical equipment of a moving vehicle is reduced. If such an interference falls into the frequency range of the spectrum 682 seen in FIG. 6b, the multiplier 540 spreads the energy of the interference to a wide band, at the same time concentrating the spectrum of the actual signal in a relatively narrow range. This results in that only a minor part of the energy of the interference remains in the band of the actual signal. Thus the spread spectrum technique, known as such, is utilized in the invention.

Figure 7:
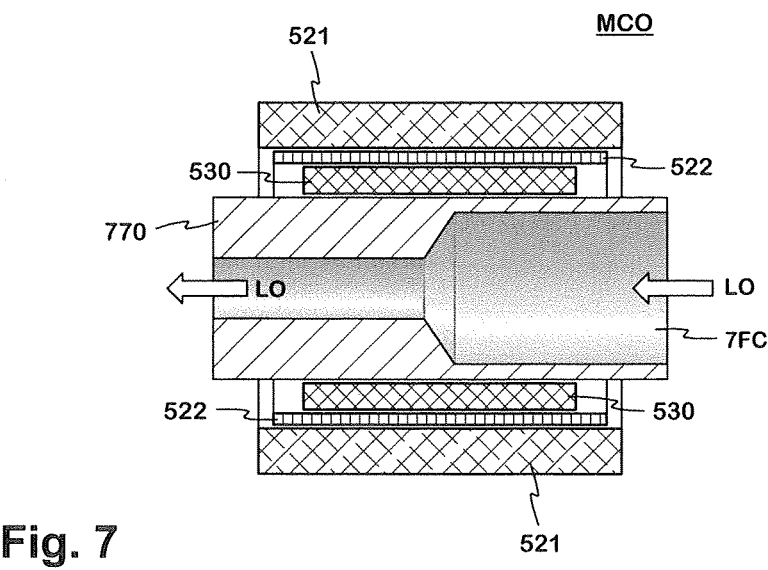
FIG. 7 presents an example of the measuring component belonging to the arrangement according to the invention.

FIG. 7 shows an example of the measuring component belonging to the arrangement according to the invention. The measuring component MCO is presented as a longitudinal section. It comprises the magnetizing winding 521, excitating winding 522, secondary winding 530 and a pipe 770, through which goes the flow channel 7FC of the medium LO. The windings are cylindrical ones and they have the same axis. The magnetizing winding is outermost, the excitating winding in the middle and the secondary winding innermost. The pipe 770 is of dielectric, magnetically inactive material, and it is located in the centre of the component so that all windings round it. In this case the magnetic flux arisen by the magnetizing and excitating windings, the changes in which induce a voltage in the secondary winding 530, goes largely through the medium LO in the flow channel.

The pipe 770 is shaped so that the cross sectional area of the flow channel 7FC changes at the middle point of the windings. This matter will be taken up anew below, in the description of FIGS. 8a, 8b. FIG. 7 has been simplified so that the connectors at the ends of the pipe 770 and also the winding frames are not visible.

Figure 8A:
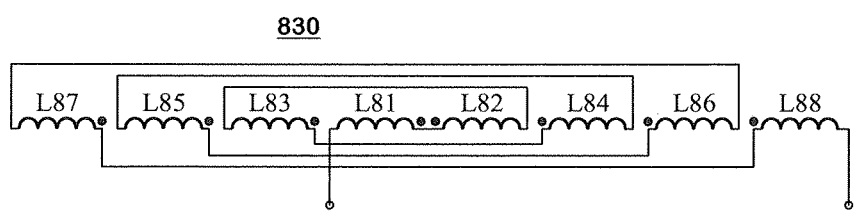
FIGS. 8a,b present an example of the gradiometric winding belonging to the arrangement according to the invention.
Figure 8B:
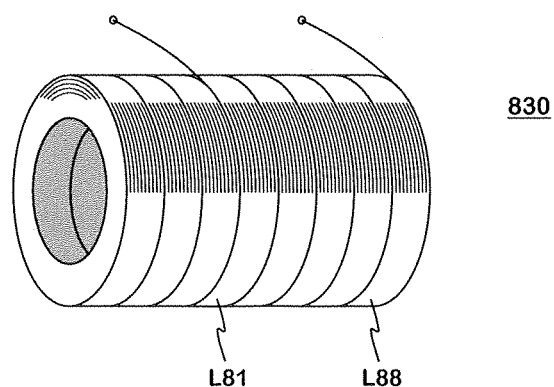

FIGS. 8a and 8b show an example of the winding belonging to the arrangement according to the invention. It can be either the secondary winding or the excitating winding, one of these windings being a customary cylindrical winding. FIG. 8a shows the principled structure of the secondary winding as a circuit diagram, and FIG. 8b shows its physical implementation. The winding 830 is a special case of so-called gradiometric coil structure, which structure comprises at least one coil pair so that the coils of the pair are similar, at a certain distance from each other on the same axis and in series, the corresponding terminals connected to each other. In this case the series circuit produces a voltage, which is proportional to the gradient of the surrounding alternating magnetic field in the direction of axis of the coils. If the gradient is zero, i.e. the field is homogenous, also the sum voltage becomes zero, because equal voltage induces in both coils.

In this example the gradiometric winding comprises four coil pairs, thus eight coils connected in series. They are located side by side and have the same outer and inner diameters. The coils of each pair are located symmetrically in respect of the middle point of the whole winding 830, the symmetry including also the fact that they are wound to opposite directions. The first L81 and second L82 coil constitute such a pair, the third L83 and fourth L84 coil constitute the second pair, the fifth L85 and sixth L86 coil constitute the third pair, and the seventh L87 and eighth L88 coil constitute the fourth pair. From the middle point of the winding 830 to one direction there are in order the first, third, fifth, and seventh coil, and from the middle point to the opposite direction there are in order the second, fourth, sixth, and eighth coil. The first coil L81 is connected to the second coil L82, the second coil to the third coil L83, the third coil to the fourth coil L84, etc. The coils of each pair are then connected in series, the corresponding terminals together.

If the above-described winding is the secondary winding, the excitating winding has a middle tap, and correspondingly, if the above-described winding is the excitating winding, the secondary winding has a middle tap. The currents in the halves of the winding with the middle tap have opposed phases, and the voltages caused by the capacitance between the excitating and secondary windings are in principle opposed in each coil pair of the gradiometric winding. (This does not require that the corresponding terminals are connected to each other.) Therefore, by means of the winding solution according to FIGS. 8a, 8b the interfering voltage in question can be lowered to a minor part comparing with the sum of the absolute values of the coil voltages. In addition, the voltage level of the response RE can be lowered, which level would otherwise be damagingly high because of the high number of turns in the secondary winding, the number being high for reducing the noise. The lowering of the voltage level of the response is based on the opposed phase of the voltages of the coils in each coil pair, and the lowering takes place also on the secondary side even in the case where the gradiometric winding is the excitating winding. The total voltage induced in the secondary winding can be made to reduce for example to the thousandth part. The actual signal, or the proportion due to the ferromagnetic particles of the total voltage of the secondary winding, is very low. In order for the actual signal not to reduce at the same time, the flow channel 7FC is made asymmetric so that its cross-sectional area changes at the middle point of the windings. In the example of FIG. 7 the cross sectional area decreases, seen in the flow direction of the medium, about to the fourth part in a relatively short distance in respect of the length of the measuring component MCO. Because of this asymmetry there are different amounts of ferromagnetic particles at the halves of the windings. The result is that the proportion due to the ferromagnetic particles in the response reduces only about 20% because of the above-described coil structure. Although the total voltage of the response reduces, as mentioned, about to the thousandth part, the actual signal proportion of it still is small. The numeral value of the proportion naturally depends on the amount of the ferromagnetic material.

FIG. 9 shows a second example of the gradiometric winding belonging to the arrangement according to the invention, which can be either the secondary winding or the excitating winding. The winding 930 comprises eight coils connected in series, which coils form four coil pairs. The first L91 and second L92 coil constitute the first pair, the third L93 and fourth L94 coil constitute the second pair, the fifth L95 and sixth L96 coil constitute the third pair and the seventh L97 and eighth L98 coil constitute the fourth pair. The coils in each pair have the same outer and inner diameters and are located side by side. The pairs, again, are located inside each other so that a layer structure is formed. The fourth pair is innermost, the third pair is on it, the second pair is on the third pair, and the first pair is outermost on the second one. The seventh L97, fifth L95, third L93 and first L91 coil are located one on the other in one half of the winding, and the eighth L98, sixth L96, fourth L94 and second L92 coil are located one on the other in the other half. The first coil is connected to the second coil in the middle of the winding, the second coil to the third coil at one end of the winding, the third coil to the fourth coil in the middle of the winding, the fourth coil to the fifth coil at the other end of the winding, etc. This results in that the voltages in the gradiometric winding, caused by the capacitance between the excitating and secondary windings, are cancelled out in the first and eighth coil, in the second and third coil, in the fourth and fifth coil and in the sixth and seventh coil. The interfering voltage in question is then brought to a minor part compared with the sum of the coil voltages.

The coils of each pair are located symmetrically from the middle plane of the whole winding 930 to the opposite directions, the symmetry including also the fact that they are wound to opposite turning directions. Therefore the part of the response, which corresponds to the magnetic field directed to the medium, is cancelled out in each coil pair. On the other hand, the actual signal, or the part of the response corresponding to the additional field caused by said magnetic field in the ferromagnetic particles, is cancelled out only for a small part because of the asymmetry of the flow channel: at one coil of each coil pair there are substantially less of ferromagnetic particles than at the other coil. In addition, the corresponding terminals of the coil pairs in different layers of the winding are arranged so that the voltages of the successive coil pairs do not cancel out but are summed.

FIG. 10 shows a second example of the measuring component belonging to the arrangement according to the invention. The measuring component MCO is presented as a longitudinal section. It comprises the magnetizing winding A21, excitating winding A22, secondary winding A30, and a dielectric pipe A70, through which goes the flow channel AFC of the medium LO, as in FIG. 7. The windings are cylindrical ones and they round the pipe A70, in which case the magnetic flux arisen by the magnetizing and excitating windings flows largely through the medium LO in the flow channel. In this example, the secondary winding is outermost, the excitating winding in the middle, and the magnetizing winding innermost.

The substantial differences to the structure presented in FIG. 7 are that the cross-sectional area of the flow channel AFC is now constant along the whole length of the component, and the magnetizing winding is shorter than the excitating and secondary windings, being located asymmetrically in respect of the middle point of the excitating and secondary windings, at one halves of these windings. A symmetric magnetizing winding would mean that also the level of the actual signal received from the secondary winding would lower very significantly, when the total level of the secondary voltage is lowered by a winding according to FIGS. 8a and 8b. In the solution according to FIG. 10 the ferromagnetic particles are magnetized in a different way at the coils of each coil pair of the gradiometric winding: at the coil which is closer to the magnetizing winding it is gone on farther to the nonlinear range than at the other coil of the coil pair. In this case the part of the actual signal received from a coil does not cancel out the part of the actual signal received from the other coil of the pair. The generating of the actual signal is based on the magnetic non-linearity.

The measuring component MCO may comprise two extra windings CL1, CL2 round the flow channel. These are marked with a dashed line in FIG. 10. If the extra windings are used, a capacitive element C is connected to the terminals of the first extra winding CL1 and a resistive element R is connected to the terminals of the second extra winding CL2. This kind of extra circuits generate quadrature components in the excitation field, which components weaken the parasitic coupling between the excitating winding and secondary winding.

FIGS. 11a and 11b show a third example of the measuring component belonging to the arrangement according to the invention. In FIG. 11a the component is presented as a cross-section and in FIG. 11b there is seen the excitating winding B22 belonging to it. In addition, the measuring component comprises a magnetizing winding B21, secondary winding B30 and a dielectric pipe B70, through which the flow channel BFC of the medium LO goes. The magnetizing winding and secondary winding are cylindrical ones and they round the pipe B70 and the excitating winding.

In this example the excitating winding B22 is two-part so that each conductor turn forms a pattern, which resembles the figure eight, in cross-section plane of the measuring component, or when viewing in the direction of the flow channel. Thus, the circulating directions of the current in these two loops are opposite. The excitating winding forms two longitudinal hollows, and the pipe B70 of the flow channel is located in one of these hollows. When there is no ferromagnetic material in the channel, the magnetic field of the excitating winding remains very weak, because the magnetic fields of its halves cancel each other out. In this case any voltage does not induce in the secondary winding. When there are ferromagnetic particles in the channel, the part of the excitating winding, which contains the flow channel, generates a stronger magnetic field than the other part, in which case some voltage induces in the secondary winding.

FIGS. 12a and 12b show another example of the gradiometric winding applicable in the arrangement according to the invention. The winding C30 is implemented by a flexible circuit board PCB. This circuit board has the shape of an elongated rectangle; in FIG. 12a it is presented as planar, and cut so that only both ends are visible. The winding conductor CNR forms a rectangular spiral, which includes in this example eight turns. The ends of the winding conductor are at the same end of the circuit board. The length of the spiral equals the length of the circuit board.

In FIG. 12b the circuit board has been rolled, whereafter the winding C30 is ready for service. Each conductor turn of the spiral constitutes a coil pair, the coils of which are in series, and in which coils the current I supplied to the winding circulates to the opposite directions. The coils, in which the current circulates to the same direction, are located side by side in one half of the cylinder. The structure thus corresponds to the structure presented in FIGS. 8a and 8b.

Figure 13:
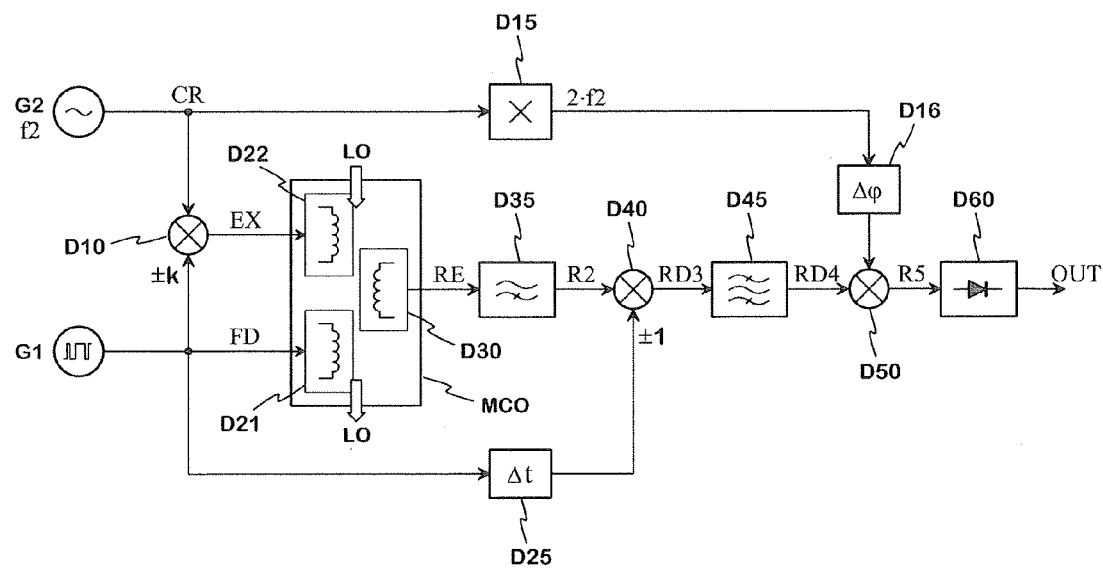
FIG. 13 presents as a block diagram a second example of the arrangement according to the invention.

FIG. 13 shows as a block diagram a second example of the arrangement according to the invention. It comprises a measuring component MCO and its feeding units as well as the processing units of the response. The electric part of the measuring component comprises the magnetizing winding D21, the excitating winding D22 and the secondary winding D30, as in FIG. 5. The feeding units comprise two signal sources and an analog multiplier. The first source G1, or the low frequency source, generates the feed FD, which is in this example a pseudorandom bipolar pulse signal. The source G1 includes e.g. a shift register fed back by 'exclusive or' ports, the clock frequency being for example 10 Hz. The source G1 is connected to the magnetizing winding D21, and the magnetic flux arising in this winding flows through the space confined by the medium LO and the secondary winding D30. The feed magnetizes during its both states the ferromagnetic particles in the medium to the nonlinear range of the magnetization curve. The second source G2, or the high frequency source, generates a 'carrier' CR. The carrier and feed are led to the multiplier D10, the output signal of which is the excitation EX. This is led to the excitating winding D22, and the magnetic field arising in this winding is summed with the magnetic field of the magnetizing winding.

The feed has in the multiplier such an attenuating coefficient k that the level of the excitation becomes for example 40 percent of the feed level. Then, like in the example of FIG. 5, the magnetic flux density in the medium corresponding to the excitation fluctuates very nonlinearly. In this case the nonlinear function is continuous, because the feed keeps, excluding the short transition times, the operating point on the magnetization curve in the nonlinear range all the time, alternately in the positive and negative part of the B-axis of the coordinates seen in FIG. 1.

The secondary winding D30 sensing the magnetic field produces the response RE. The secondary winding is connected to a high-pass filter D35, the boundary frequency of which is above the significant part of the spectrum of the feed. The output of the high-pass filter is connected to the second multiplier D40, to the other input of which is connected the feed FD through a delay unit D25. The feed is delayed so that its state transitions take place precisely simultaneously with the phase hops in the output signal R2 of the high-pass filter. The second multiplier D40 removes from the response the sudden transitions occurring at random intervals, for which reason in its output signal, or the multiplication signal RD3, the spectrum of the actual signal is remarkably narrower than in the input signal R2 of the multiplier. At the same time the spectrum of the narrowband interferences, which possibly occur in the signal R2, spreads because they naturally are not synchronized with the feed. This results in that only a minor part of the energy of an interference remains in the narrow band of the actual signal. The function of the second multiplier is then same as of the multiplier D40 in FIG. 5.

The output of the multiplier D40 is connected to a bandpass filter D45, which produces the actual signal RD4. The centre frequency of the passband of the bandpass filter is 2f2. Thus the part of the excitation's spectrum around the frequency 2f2 is chosen for further processing, because this part arises only if there is magnetically nonlinear material in the medium. In addition, the interference due to stray capacitance occurring at the carrier frequency is avoided. The output of the bandpass filter is connected the third multiplier D50. This functions as a detector for the 'modulation', which is caused by the nonlinear medium to the signal. The 'subcarrier' for the third multiplier D50 is generated from the carrier CR by means of a frequency multiplier D15 and phase shifter D16. The frequency multiplier, which includes also a bandpass filter with the centre frequency of 2f2, produces a sine wave with this frequency, the phase of which sine wave is tuned by the phase shifter D16 to the same one as the phase of the component with frequency 2f2 in the actual signal RD4. The third multiplier D50 shifts the spectrum around the frequency 2f2 to the baseband. The output of the multiplier is connected to a level measuring circuit D60, which produces a DC signal proportional to the level of the output signal R5 of the third multiplier D50. This DC signal is the output signal OUT of the whole measuring arrangement.

Figure 14:
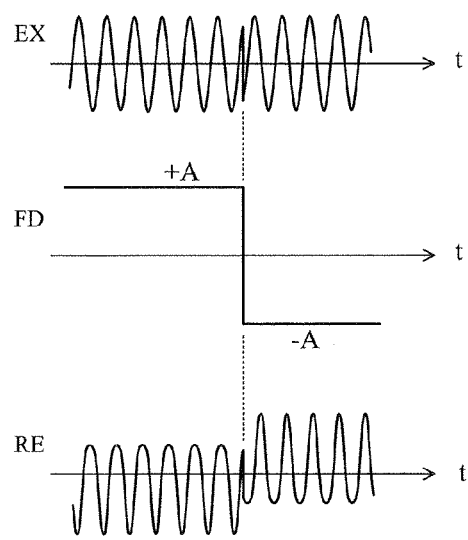
FIG. 14 presents in the time domain the principled input and output signals of the measuring component in the arrangement according to FIG. 10.

In FIG. 14 there is in the time domain a principled presentation of the input signals FD and EX and output signal RE of the measuring component in the arrangement according to FIG. 13. One state transition of the feed is seen in FIG. 14; a change in its current from the value +A to value −A. Such changes occur in the feed at random intervals. In practice the state transition of the feed takes a little time, because the current of an inductance cannot change abruptly. The excitation EX has the shape of the carrier CR before and after the state transition of the feed. At each transition moment the phase of the excitation changes to the opposed one because of the change of the sign. The response RE has been drawn without interferences and noise. Before the feed's state transition the operating point in the HB coordinates is located in the upper nonlinear range of the magnetization curve of the ferromagnetic particles, in which case the positive half cycles of the sinusoidal excitation flatten. After the feed's state transition the operating point is located in the lower nonlinear range of the magnetization curve of the ferromagnetic particles, in which case the negative half cycles of the excitation flatten.

A system according to the invention has been described above. The implementation way for the part of both the method and arrangement can naturally differ in detail from the ones presented. For example the feed, which magnetizes the ferromagnetic particles to a nonlinear range, can also be a triangular wave, the fundamental frequency of which is f1. In this case, the harmonics of the frequency 2f1 in the spectrum of the response, in respect of the centre frequency f2 of the excitation, and the parts of the spectrum, which correspond to those harmonics, are lower than in the case when a sinusoidal feed is used. This means that in comparison to the case of FIG. 5 the portion of the actual signal of the response's energy is higher, the signal-to-noise ratio and the accuracy of the measurement being thus improved. In addition, the internal losses of a triangular wave generator are lower than of a sine wave generator, which may be significant when the measuring system has been mounted in a vehicle. The structure and location of the windings as well as the shape of the medium's flow channel can vary. The windings can be implemented also by a broad foil so that they have only one turn, for example. Randomness can be only in the feed of the signals magnetizing the ferromagnetic particles when the excitation is sinusoidal. The inventive idea can be applied in different ways within the scope set by the independent claims 1 and 13.

The invention claimed is:

1. An arrangement for quantifying the proportion of ferromagnetic particles in a medium, which arrangement comprises:
   a flow channel for the medium;
   a low frequency source, which is a sine wave generator or a triangle wave generator, to generate a feed for basic magnetization of the ferromagnetic particles;
   a high frequency source to generate an excitation for additional magnetization of the ferromagnetic particles, said high frequency source being connected to a carrier input of a modulator, in which case an output signal of the modulator is the excitation;
   a magnetizing winding round said flow channel, connected to the low frequency source, to generate a magnetic field in the medium;
   an excitating winding to be fed by the excitation round said flow channel to generate an additional magnetic field in the medium;
   a secondary winding functioning as a sensor of the magnetic field to measure change in the magnetic flux density of the medium, or to generate a response; and
   means for separating, a part from the response which is due to the magnetic non-linearity of the medium,
   wherein the arrangement further comprises means for generating the excitation from numerous frequency components so that a spectrum of the arrangement is wide in respect of spectra of typical interferences and at least nearly continuous, said means for generating the excitation comprising a third source, the output signal of which is a random signal and the third source being, connected to a modulation input of the modulator, and said means for separating from the response the part due to the magnetic non-linearity of the medium comprise after the secondary winding in order:
   a high-pass filter to remove low frequency parts from the response;
   a multiplier, to one input of which is connected through a delay unit a circuit feeding the excitating/magnetizing winding, and a bandpass filter to generate an actual signal; and
   a detector, to carrier input of which is connected the low/high frequency source through a frequency multiplier and phase shifter, to generate an output signal.

2. An arrangement according to claim 1, wherein said modulator is a frequency modulator.

3. An arrangement according to claim 1, wherein the circuit connected to one input of said multiplier through the delay unit is the circuit feeding the excitating winding, or the output stage of the modulator.

4. An arrangement according to claim 3, wherein the source connected to carrier input of said detector through the frequency multiplier and phase shifter is the low frequency source, and an output of the detector is connected to a low-pass filter to produce the output signal with the shape of direct voltage.

5. An arrangement according to claim 1, wherein the low frequency source is a venerator producing binary random signal, and said means for generating the excitation further comprise a multiplier, to one input of which is connected said high frequency source and to another input the low frequency source for inverting randomly the sine wave of the high frequency source, in which case the output signal of the multiplier is the excitation.

6. An arrangement according to claim 1, wherein the circuit connected to one input of said multiplier through the delay unit is the circuit feeding the magnetizing winding, or the low frequency source.

7. An arrangement according to claim 6, wherein the source connected to carrier input of said detector through the frequency multiplier and phase shifter is the high frequency source, and an output of the detector is connected to a level measuring circuit to produce the output signal with the shape of direct voltage.

8. An arrangement according to claim 1, wherein the magnetizing winding, excitating winding and secondary winding are cylindrical windings inside each other, which all round a pipe forming the flow channel, and the secondary winding or excitating winding is a gradiometric winding.

9. An arrangement according to claim 8, wherein the medium's flow channel is asymmetrical so that its cross-sectional area changes at the middle point of the windings to make the amount of the ferromagnetic particles different at the halves of the windings in a measuring situation.

10. An arrangement according to claim 9, wherein for eliminating the parasitic voltage and reducing total voltage of the response said gradiometric winding comprises mechanically parallel and electrically serial coils, which constitute coil pairs so that the two coils of each pair are located at the same distance from the middle point of said winding and their corresponding terminals are connected to each other, and the other coil of the excitating and secondary windings is a customary winding with a middle tap.

11. An arrangement according to claim 9, wherein for eliminating the parasitic voltage and reducing total voltage of the response said gradiometric winding comprises coil pairs, in each of which the coils are mechanically parallel and the corresponding terminals connected to each other, and the coil pairs are one on the other and electrically in series so that the voltages of the coil pairs are summed.

12. An arrangement according to claim 8, wherein the cross-sectional area of the medium's flow channel is constant, and the magnetizing winding is shorter than the excitating winding and secondary winding, and is located asymmetrically in respect of the middle point of the excitating and secondary windings to magnetize the ferromagnetic particles by different strength at the coils of each coil pair of the gradiometric winding.

13. An arrangement according to claim 12, wherein there are two extra windings round the flow channel, a capacitive element being connected to the terminals of the first extra winding and a resistive element being connected to the terminals of the second extra winding.

14. An arrangement according to claim 1, wherein the magnetizing winding and the secondary winding are cylindrical windings inside each other, which round a pipe and the excitating winding forming the flow channel, each conductor turn of the excitating winding forming, when viewing in the direction of the channel, a pattern which resembles the figure eight so that the circulating directions of the current to be supplied to the excitating winding in these two loops are opposite, and the excitating winding forms two longitudinal hollows, the pipe of the flow channel being located in one of these hollows.

15. An arrangement according to claim 8, wherein said gradiometric winding is implemented by a rolled flexible circuit board, which circuit board comprises, when planar, a winding conductor with the shape of a rectangular spiral, the ends of the winding conductor being at the same end of the circuit board, and the length of the spiral being substantially the same as the length of the circuit board.

16. A method for quantifying the proportion of ferromagnetic particles in a medium, in which method comprises:
- a low frequency sinusoidal or triangular signal, or feed, is generated, by which a magnetic field is arisen in a medium to magnetize ferromagnetic particles in the medium to nonlinear range of the magnetization curve;
- a high frequency signal compared with the feed, or an excitation, is generated by which an additional magnetic field is arisen in the medium, said excitation being produced by modulating a carrier generated by a high frequency source by a random signal;
- changes in the magnetic flux density are measured; and
- a part due to the magnetic non-linearity of the medium is separated from a signal, or response (RE), produced by measuring,
- wherein the excitation is generated from numerous frequency components so that a spectrum of the excitation is at least nearly continuous and wide in respect of spectra of typical interferences, and for separating from the response the part due to the magnetic non-linearity of the medium;
- low frequency parts are removed from the response through filtering;
- the filtered response is multiplied by a delayed excitation signal that has ails the magnet field, which signal includes the same random fluctuation as the response;
- the part due to said non-linearity is detected from the signal obtained above, or the multiplication signal, to produce an actual output signal by removing from said multiplication signal by filtering the frequency components apart from frequency components in a certain range round the frequency 2f1, where f1 is the fundamental frequency of the feed.

17. A method according to claim 16, wherein the frequency of said carrier is modulated using a modulation index, which causes a substantially wider spectrum of the excitation compared to the spectrum of said random signal.

18. A method according to claim 16, wherein an output signal is produced from the actual signal by detecting using a sine wave with the frequency 2f1 as a subcarrier, the sine wave phased so that its phase is the same as the phase of the component with frequency 2f1 in the actual signal, and by filtering the obtained detecting result so that an output signal with the Shape of direct voltage is left.

19. A method according to claim 16, wherein said feed is generated to be a binary random signal, and the excitation is produced by inverting a carrier generated by a high frequency source whenever the state of the feed changes.

20. A method according to claim 19, wherein said signal generating the magnet field, by which signal the filtered response is multiplied, is the delayed feed, and an actual signal is produced by removing from said multiplication signal by filtering the frequency components apart from frequency components in a certain range round the frequency 2f2, where f2 is the fundamental frequency of the carrier.

21. A method according to claim 20, wherein an output signal is produced from the actual signal by multiplying it by a sine wave with the frequency 2f2 phased so that its phase is the same as the phase of the component with frequency 2f2 in the actual signal, and by measuring the level of the signal obtained by multiplying.

* * * * *